United States Patent
Bock et al.

(10) Patent No.: US 10,168,471 B2
(45) Date of Patent: Jan. 1, 2019

(54) OPTICAL SENSOR AND METHOD

(71) Applicants: Wojtek J. Bock, Ottawa (CA); Saurabh Mani Tripathi, Gatineau (CA); Predrag Mikulic, Ottawa (CA)

(72) Inventors: Wojtek J. Bock, Ottawa (CA); Saurabh Mani Tripathi, Gatineau (CA); Predrag Mikulic, Ottawa (CA)

( * ) Notice: Subject to any disclaimer, the term of this patent is extended or adjusted under 35 U.S.C. 154(b) by 289 days.

(21) Appl. No.: 13/789,760

(22) Filed: Mar. 8, 2013

(65) Prior Publication Data

US 2014/0254977 A1    Sep. 11, 2014

(51) Int. Cl.
- *G02B 6/02*     (2006.01)
- *G01D 5/353*    (2006.01)
- *G01N 21/77*    (2006.01)

(52) U.S. Cl.
CPC ..... *G02B 6/02085* (2013.01); *G01D 5/35316* (2013.01); *G01N 21/7743* (2013.01)

(58) Field of Classification Search
None
See application file for complete search history.

(56) References Cited

U.S. PATENT DOCUMENTS

| | | | | |
|---|---|---|---|---|
| 5,864,641 | A * | 1/1999 | Murphy et al. | 385/12 |
| 6,021,240 | A * | 2/2000 | Murphy et al. | 385/37 |
| 6,652,808 | B1 * | 11/2003 | Heller | B01J 19/0046 257/E21.43 |
| 7,837,663 | B2 * | 11/2010 | MacDonald | A61F 13/42 128/206.21 |
| 2005/0105841 | A1 * | 5/2005 | Luo et al. | 385/12 |
| 2007/0025661 | A1 * | 2/2007 | Wang et al. | 385/37 |
| 2007/0116401 | A1 * | 5/2007 | Xia et al. | 385/12 |
| 2009/0263072 | A1 * | 10/2009 | Albert et al. | 385/13 |
| 2011/0085759 | A1 * | 4/2011 | Lee | G01N 21/7703 385/12 |
| 2011/0228275 | A1 * | 9/2011 | Xia | G01N 21/77 356/437 |

OTHER PUBLICATIONS

Han et al., "Shift and splitting of resonant peaks in long-period fiber gratings for sensing applications", 2001, Optical fiber communication conference and Exhibit OFC 2001.*

James et al., "Optical fibre long-period grating sensors: characteristics and application", 2003, Measurement Science and Technology 14 (2003) R49-R61.*

(Continued)

*Primary Examiner* — Chad H Smith

(57) ABSTRACT

An optical sensor has a waveguide having a core, a cladding having an outer surface and a long period fiber grating. The core, the cladding and the long period fiber grating collectively provide at least two resonant wavelengths. The optical sensor also has binding sites on the outer surface of the cladding for binding to elements to be detected to the outer surface of the cladding. The cladding may be thinned down to a thickness sufficiently low produce the resonant wavelengths. The binding sites include agents for binding to the elements to be detected with the agents being covalently bonded to the surface of the cladding. Example binding sites can include bacteriophages for detecting *E. coli* bacteria, Palladium for detecting hydrogen, or synthetic DNA for detecting viruses of certain molecules for example.

12 Claims, 8 Drawing Sheets

(56) References Cited

OTHER PUBLICATIONS

Tripathi et al., "Refractive index sensing characteristics of dual resonance long period gratings in bar and metal-coated D-shaped fibers", 2009, Applied Optics, Nov. 2009, vol. 48, No. 31.*
Garg et al., "Long period fiber grating based temperature-compensated high performance sensor for bio-chemical sensing applications", Sensors and Actuators B, 176 (2013) 1121-1127.*
Pilla et al. A protein-based biointerfacing route toward label-free immunoassays with long period gratings in transition mode, Biosensors and Bioelectronics 31 (1) (2012) 486-491.*

* cited by examiner

OPTICAL SENSOR AND METHOD

TECHNICAL FIELD

The present disclosure relates to optical sensors for detection of elements.

BACKGROUND

Pathogenic *Escherichia coli* (*E. coli*) bacteria are one of the most dangerous agents of food-borne disease. Consumption of contaminated food or water can be deadly, especially for children and the elderly. Although *E. coli* bacteria infections are most common in developing countries, many recent outbreaks in Europe and Northern America have been attributed to a strain of *E. coli* bacteria which has been identified among the most common causes of diseases related to food safety. Accurate routine testing is crucial for outbreak prevention.

There are available techniques for detecting *E. coli* bacteria. The current techniques require time-consuming amplification of samples and the standard detection process of *E. coli* bacteria takes about 24 hours to obtain results from culturing methods. Although more recent detection techniques such as PCR (Polymerase Chain Reaction), ELISA (Enzyme Linked Immuno-Sorbent Assay) and IMS (Ion Mobility Spectrometry) offer a more rapid detection, an analysis time of several hours is still required. For the specific and rapid detection of such pathogens, bio-recognition elements such as antibodies, nucleic acids (DNA/RNA) and bacteriophages have widely been used for the specific capturing of the target bacteria. Their binding can be detected by fluorescence labeling methods or by label-free methods. Each of these recognition elements has its own advantages and disadvantages. For example, recognition based on nucleic acid, though offering high specificity, suffers from the inability to discriminate between viable and non-viable cells. For antibody-based recognition elements, the drawbacks are high manufacturing cost, lack of stability/repeatability in measurements and cross-binding to other bacteria which may result in false positives.

SUMMARY

According to a first broad aspect, provided is an optical sensor. The optical sensor has a waveguide having a core, a cladding having an outer surface and a long period fiber grating. The core, the cladding and the long period fiber grating collectively provide at least one split resonance. The optical sensor also has binding sites on the outer surface of the cladding for binding to elements to be detected to the outer surface of the cladding.

In some embodiments, the cladding is thinned down to a thickness sufficiently low to produce the double resonant wavelength(s).

In some embodiments, the binding sites include agents for binding to the elements to be detected, the agents being covalently bonded to the surface of the cladding.

In some embodiments, the binding sites include a biophage.

In some embodiments, the binding sites include a bacteriophage.

In some embodiments, the binding sites include Palladium.

In some embodiments, the binding sites include synthetic DNA.

In some embodiments, the binding sites include at least two different types of binding sites capable of binding to different types of elements.

According to a second broad aspect, provided is an optical sensor having a waveguide having a core, a cladding having an outer surface and a long period fiber grating. The core, the cladding and the long period fiber grating collectively provide at least one resonant wavelength. The optical sensor also has binding sites covalently bonded on the outer surface of the cladding for binding to elements to be detected to the outer surface of the cladding.

According to a third broad aspect, provided is a method of fabricating an optical sensor having a waveguide with a core, cladding having an outer surface and a grating. The method involves etching the cladding at the outer surface to thin the cladding down to a thickness sufficiently low to produce at least one split resonance.

According to a fourth broad aspect, provided is a method of fabricating an optical sensor having a waveguide with a core, cladding having an outer surface and a grating. The method involves covalently bonding binding sites to the outer surface of the cladding for allowing elements to be detected to bind to the outer surface of the cladding.

BRIEF DESCRIPTION OF THE DRAWINGS

The features and advantages will become more apparent from the following detailed description of the preferred embodiment(s) with reference to the attached figures, wherein.

DETAILED DESCRIPTION OF THE PREFERRED EMBODIMENTS

Figure 1:
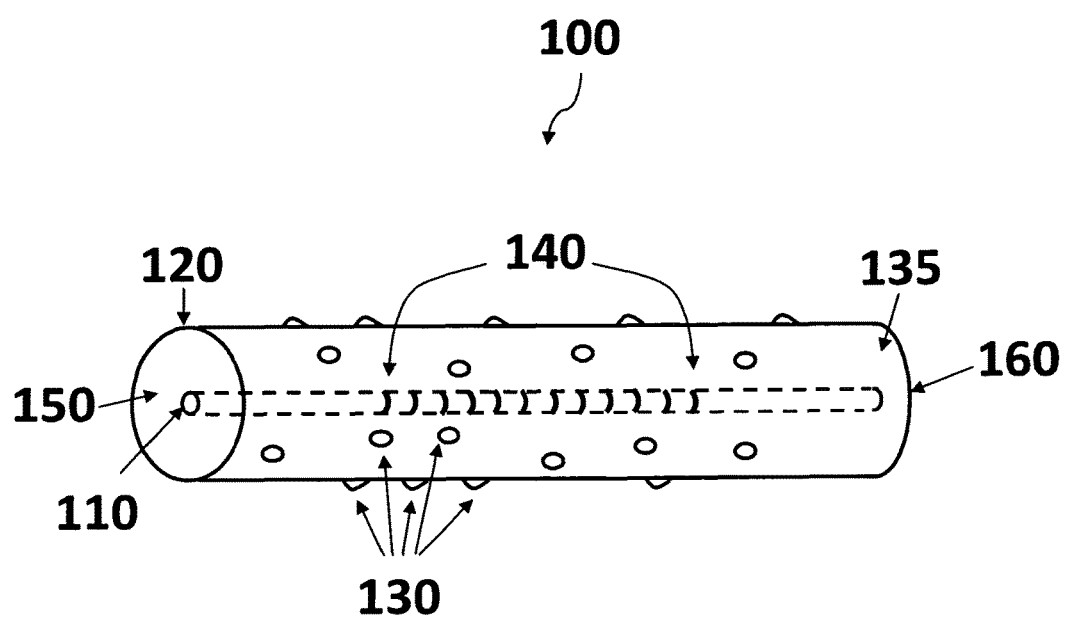
FIG. 1 shown is a perspective view of an optical sensor for use in detecting *E. coli* (Pathogenic *Escherichia coli*) bacteria, in accordance with an embodiment.

Optical sensors can be used to detect bioagents, pathogens, and more generally other elements to be detected. Referring to FIG. 1, shown is a perspective view of an optical sensor, generally indicated by 100, for use in detecting *E. coli* (Pathogenic *Escherichia coli*) bacteria, in accordance with an embodiment. The optical sensor 100 has a core 110 and cladding 120. Binding sites 130 are located on a surface 135 of the cladding 130. Only a few binding sites 130 are identified to avoid cluttering FIG. 1. The core 110 has a grating 140. The optical sensor 100 also a first end 150 and a second end 160.

During use the first end 150 of the optical sensor 100 is coupled to a broadband light source (not shown) and the second end 160 of the optical sensor 100 is coupled to a detector for detecting the light transmitted through the optical sensor 100. For the detection of E. coli bacteria the binding sites 130 are a biophage to which E. coli bacteria can bind. The optical sensor 100 is immersed in a solution and, if present in the solution, E. coli bacteria will bind to the binding sites and change the optical properties of the optical sensor 100. More particularly, the transmittance of the optical sensor will be affected by the presence of E. coli bacteria bound to the surface 135 of the cladding 130 and this change in the transmittance will be detected by the detector.

The period of the grating 140 can vary. However, the periodicity can be as low as of the order of 150 µm for LPFGs (Long Period Fiber Gratings). Creating a grating with such a small periodicity is not cost effective given the currently available techniques. Furthermore, binding sites 130 or biophage are fixed to the surface 135 of the cladding 120 through an adsorption process or through covalent bonding. Advantageously, with covalent bonding, the biophage is strongly coupled to the surface 135 and does not detach from the surface 135 resulting in stability of the optical sensor 100.

Figure 2A:
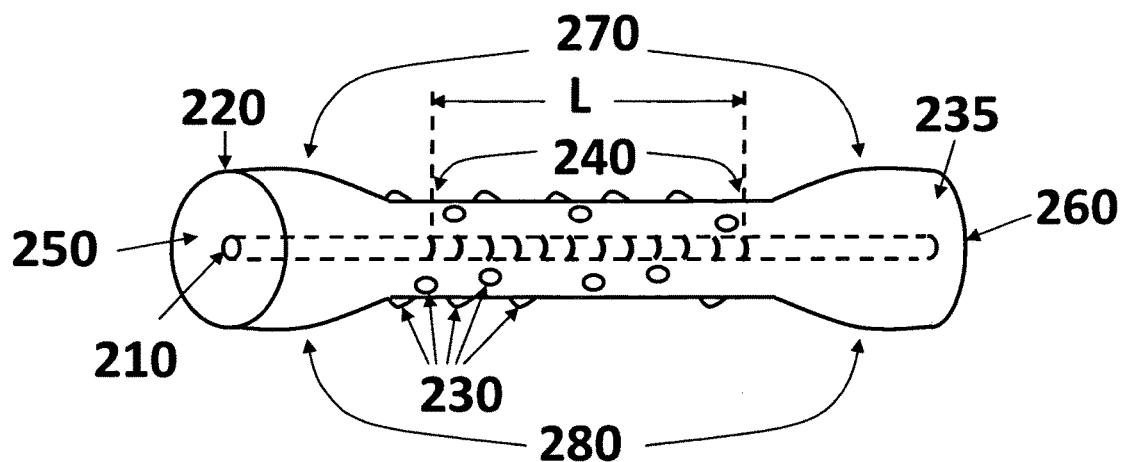
FIG. 2A is a perspective view of an optical sensor for use in detecting *E. coli* bacteria, in accordance with another embodiment.
Figure 2B:
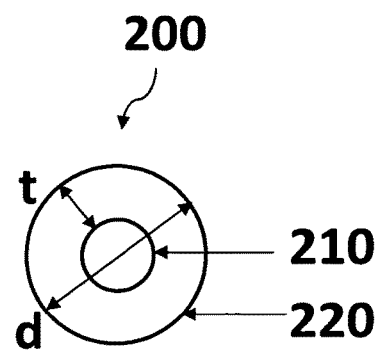
FIG. 2B is cross-sectional view of the optical sensor of FIG. 2A.
Figure 3:
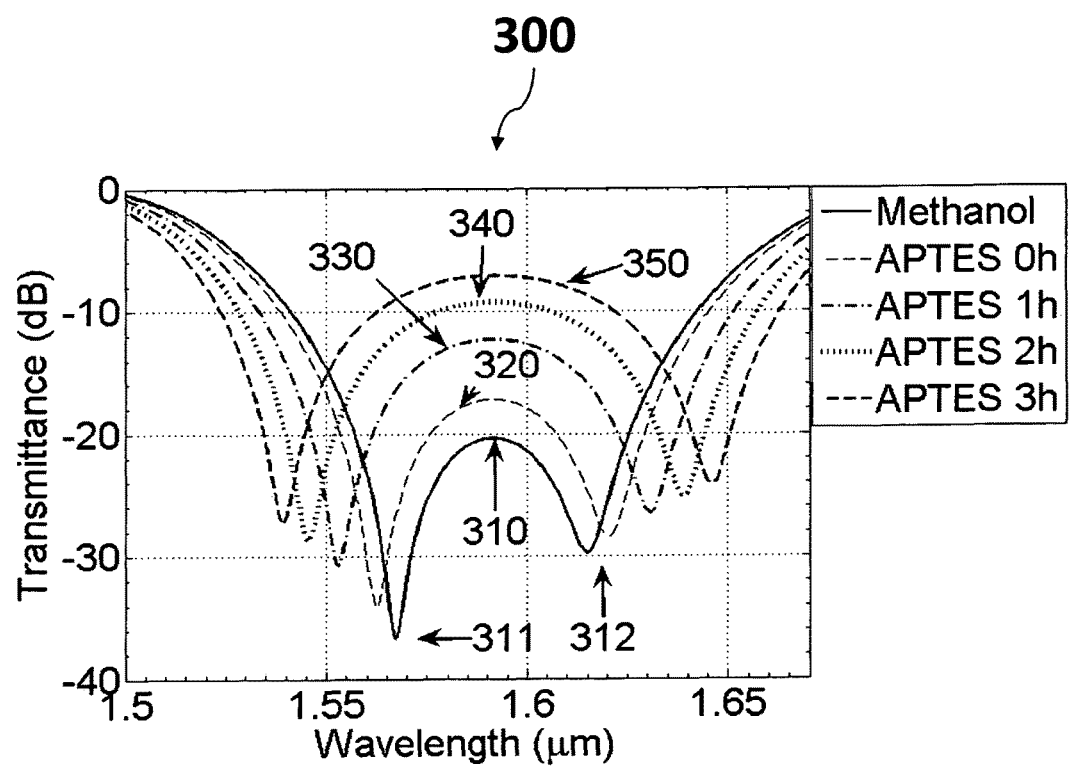
FIG. 3 is a plot of the transmittance of the optical sensor of FIG. 2A plotted as a function wavelength of light propagating through the optical sensor.

Referring to FIG. 2A, shown is a perspective view of an optical sensor, generally indicated by 200, for use in detecting E. coli bacteria, in accordance with an embodiment. The optical sensor 200 has a core 210 and cladding 220. Binding sites 230 are located on an outer surface 235 of the cladding 220. Only a few binding sites 230 are identified to avoid cluttering FIG. 2A. The core 210 has a grating 240. The cladding 220 has a recessed portion 270 where the thickness of the cladding 220 is reduced. FIG. 2B shows a cross-section of the optical sensor 200 through the recessed portion 270 of the optical sensor 200. The cross-section of the optical sensor 200 in FIG. 2B shows the cladding having a diameter d and thickness t. The optical sensor 200 also a first end 250 and a second end 260. The grating 240 is a LPFG (Long Period Fiber Grating). A LPFG is created by generating periodic variations in the core 210 and/or the cladding 220 of the optical sensor 200 in order to redirect part of an optical field from the core 210 to the cladding 220. LPFGs are different from Bragg gratings in that the periodicity of the index of refraction of the index of refraction in the core and core cladding is of the order for 100 times longer than for Bragg gratings. Advantageously, the manufacturing process for generating LPFGs is more cost effective than that of Bragg gratings due to the larger spatial dimensions. In the embodiment of FIGS. 2A and 2B the optical fiber 200 has undergone an etching process in which a portion 280 of the outer surface 235 of the cladding 220 has been etched away to create the recess 270 resulting in a thinning of the cladding 220. The use of an LFPG and a reduced thickness t of the cladding results in a split resonance with wavelengths $\lambda_{R1}$ and $\lambda_{R2}$ in at which the transmittance of the optical sensor is at a minimum. FIG. 3 is a plot, generally indicated by 300, of the transmittance of the optical sensor 200 of FIG. 2A plotted as a function wavelength of light propagating through the optical sensor 200. More particularly, the plot 300 has a curve 310 for the case when the optical sensor is immersed in Methanol. The curve 310 shows two resonance wavelengths 311, 312.

An exemplary method of manufacturing the optical sensor 200 will now be described. In this exemplary method a single mode optical fiber is used. For example a SMF-28™ waveguide manufactured by Corning N.Y., 14831 USA, is selected as a waveguide for the optical sensor 200. The photosensitivity of the waveguide is increased by hydrogen loading the waveguide at 150 bars in a hydrogen chamber for 15 days. The waveguide has a core and cladding and a photosensitive LPFG is inscribed into the core using a chromium amplitude mask with a pitch of 226.8 µm and a high-power KrF excimer laser (Lumonics™ Lasers: Pulse Master®-840) emitting at 248 nm at a pulse repetition rate of 100 Hz and with pulse duration of 12 ns and peak pulse energy of 10 mJ. Another possible method to fabricate gratings is arc-discharge. The waveguide is then annealed at 150° C. for 3 hours to release the excess hydrogen to stabilize the optical properties of the waveguide.

Decreasing the thickness d of the cladding 220 of the optical sensor 200, by way of the above etching process for example, results in the grating being tuned. More particularly, the etching process results in a split resonance with two resonance wavelengths $\lambda_{R1}$ and $\lambda_{R2}$ in the low loss window of telecommunication wavelengths for air as a surrounding medium. Etching provides an efficient way to get the split resonance. Furthermore, it is to be clearly understood that reducing the thickness of the cladding etching is only one way to achieve a split resonance and for example an optical sensor can be manufactured with the appropriate thickness required for a split resonance. More generally, the number of split resonances can be controlled by controlling the reducing the thickness of the cladding and/or changing the modulation amplitude of the laser light used for creating the grating.

A specific resonance wavelength ($\lambda_{Ri}$) is expressed as $$\lambda_{Ri} = \Lambda\left(n_{effi}^{c} - n_{effi}^{cl} + \frac{(\kappa_{c-c} - \kappa_{cl-cl})}{k_0}\right)$$

where $n_{effi}^{c}$ and $n_{effi}^{cl}$ are the effective refractive indices of the core 210 and the cladding 220, respectively, for mode i; $\Lambda$ is the period of the grating 240; and $K_{c-c}$ and $K_{cl-cl}$ are the coupling coefficients of the core 210 and the cladding 210, respectively. In the exemplary optical sensor 200, the 11$^{th}$ order cladding mode ($LP_{011}$) is excited using a grating period of 226.8 µm over a length L of 4 cm.

Is to be clearly understood that the optical sensor 200 of FIGS. 2A and 2B, need not be fabricated from an SMF-28™ waveguide and that other types of waveguides are possible. For example, other possible waveguides include but are not limited to multimode fibers, polarization maintaining fibers, gradient index fibers, tapered fibers, photonic crystal fibers, holey fibers, birefringent fibers, planar ridge waveguides, planar strip waveguides, sub-wavelength grating waveguides, photonic crystal waveguides and photonic crystal defect waveguides. Furthermore, it is to be clearly understood that the grating 240 of the optical sensor 200 need not be impressed in the core 210. More generally, the grating 240 is impressed in the core 210 only, the cladding 220 only, or both the core 210 and the cladding 220. In the embodiment of FIG. 2A the grating 240 is oriented perpendicular to the direction of propagation of light and in some other embodiments the grating 240 is tilted or angled relative to the direction of propagation of light.

With reference to FIG. 2A, an exemplary method of creating the binding sites 230 on the outer surface 235 of the cladding 220 will now be described. *E. coli* bacteria is first cultured. For example, a frozen stock of *E. coli* bacteria is used to seed Luria-Bertani (LB) media overnight. The *E. coli* bacteria are then harvested by centrifugation at 3000 g for 10 minutes, followed by washing in a phosphate-buffered saline (PBS) buffer. Dilutions of the overnight culture are plated on LB agar to determine the titer, expressed in colony forming units (cfu). Appropriate dilutions of bacteria stock are made in the PBS (Phosphate-Buffered Saline) buffer from the overnight culture stock. A T4-bacteriophage is then prepared. To produce a stock of T4-bacteriophage solution, 100 µL of *E. coli* log-phase culture is added to 3 ml of cooled top agar and the mixture is poured onto an LB agar plate until it solidifies. 100 µL of phage stock (T4 phage) specific to *E. coli* bacteria is then added to the solidified top agar and incubated at 37° C. overnight to create a lawn of bacteria. A macroplaque is developed on the lawn of bacteria after incubation. A top agar is then scrapped off with 3 ml of lambda buffer, the suspension or liquid containing the *E. coli* bacteria is collected in a 50 ml centrifuge tube, followed by an additional washing of the LB agar plate with another 3 ml of lambda buffer. Three drops of chloroform are then added to the suspension, which is then vortexed and centrifuged at 3500 g for 10 minutes. The phage containing supernatant is then filtered through a 0.22 µm filter to remove bacterial debris. The titer of the phage stock is determined by serial dilution of the stock. The bacteriophages are then immobilized.

As discussed above, in the preferred embodiment of FIG. 2A, the binding sites 230 are covalently bonded to the outer surface 235 of the cladding 220. An exemplary process of covalently bonding the binding sites 230 to the cladding 220 will now be described. In this example, bacteriophages are covalently bonded to the outer surface 135 of the cladding 220. As discussed above, a SMF-28™ waveguide is used to produce the optical sensor 200, and such a device has silica as a material for the cladding 220. The outer surface 235 is silanized by incubating the cleansed optical sensor 200 in a solution containing 3-Aminopropyltris(trimethylsiloxy)silane (APTES) $H_2N-(CH_2)_3-Si-(OCH_3)_3$ and Methanol for 3 hours. The solution includes a 5% concentration of 3-Aminopropyltris(trimethylsiloxy)silane (APTES) $H_2N-(CH_2)_3-Si-(OCH_3)_3$. This process produces a mono-layer or multi-layer poly silane film covalently bonded to the silica on the outer surface 235 of the cladding 220 with the amino functional groups of the 3-Aminopropyltris(trimethylsiloxy)silane (APTES) $H_2N-(CH_2)_3-Si-(OCH_3)_3$ exposed on top of the film. The optical sensor 220 is then rinsed in methanol and then further rinsed in deionized water. The amino functional groups that are exposed on the top of the film are functionalized by an amine-reactive homo-bifunctional cross-linker glutaraldehyde. More particularly, the optical sensor 200 is immersed for 30 minutes in a solution containing 5% concentration of the glutaraldehyde in deionized water in order to activate the amino functional groups on the top of the film at the outer surface 235 for with the T4 bacteriophages. The optical sensor 200 is then rinsed with deionized water to remove the excess glutaraldehyde and further rinsed with a PBS buffer to neutralize the surface to pH 7.5. With the outer surface 135 being activated, the optical sensor 200 is then immersed in a T4 bacteriophage solution ($10^{10}$ pfu/ml) for 4 hours in order to covalently bond the T4 bacteriophages to the amino functional groups that are exposed at the outer surface 235 thereby forming the binding sites 230 for the *E. coli* bacteria. The optical sensor 200 is then immersed in a solution containing BSA (Bovine Serum Albumin) (1 mg/ml) for 30 minutes to block sites which are not covered with bacteriophages on the outer surface 235 of the cladding 220. The BSA is then removed by washing the optical sensor 200 in a PBS buffer.

The presence of the APTES has an effect on the transmittance of the optical sensor. With reference to FIG. 3, the plot 300 shows a curve 310 for the transmittance as a function of wavelength when the optical sensor is immersed in Methanol. The plot 300 also shows curves 320, 330, 340, 350 which represent the transmittance of the optical sensor as a function of wavelength when the optical sensor 220 is immersed in a solution of 5% concentration of 3-Aminopropyltris(trimethylsiloxy)silane (APTES) $H_2N-(CH_2)_3-Si-(OCH_3)_3$ in Methanol for 1 min, 1 hr, 2 hrs, and 3 hrs, respectively. The curves 320, 320, 330, 340, 350 show a change in the transmittance when the outer surface is exposed to the 3-Aminopropyltris(trimethylsiloxy)silane (APTES) $H_2N-(CH_2)_3-Si-(OCH_3)_3$ or equivalently when the APTES accumulates on the outer surface 235.

In this example, the binding sites 230 are formed using T4 bacteriophages which are used to bind to *E. coli* bacteria. When immersed in a solution containing *E. coli* bacteria the *E. coli* bacteria will bind to the T4 bacteriophages thereby changing the transmittance of the optical sensor 200. Furthermore, the amount of *E. coli* bacteria that binds to the binding sites 230 depends on the concentration of the *E. coli* bacteria in solution. Therefore, given that the transmittance is affected by the amount of *E. coli* bacteria bound to the outer surface 235 of the cladding 220 the transmittance also depends on the concentration of *E. coli* bacteria in solution.

Figure 4:
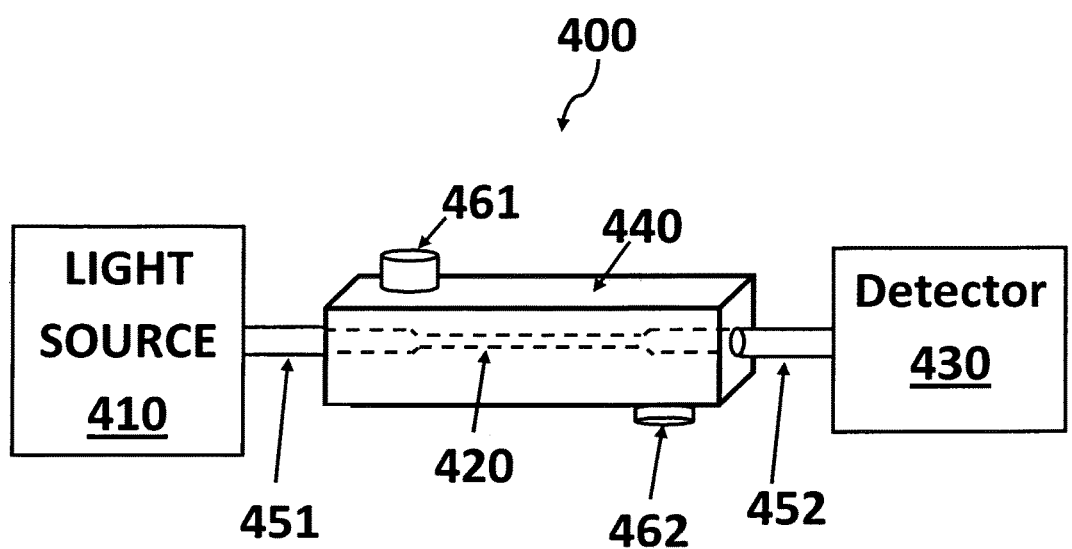
FIG. 4 is a functional block diagram of a system for detecting an element to be detected, in accordance with another embodiment.
Figure 5:
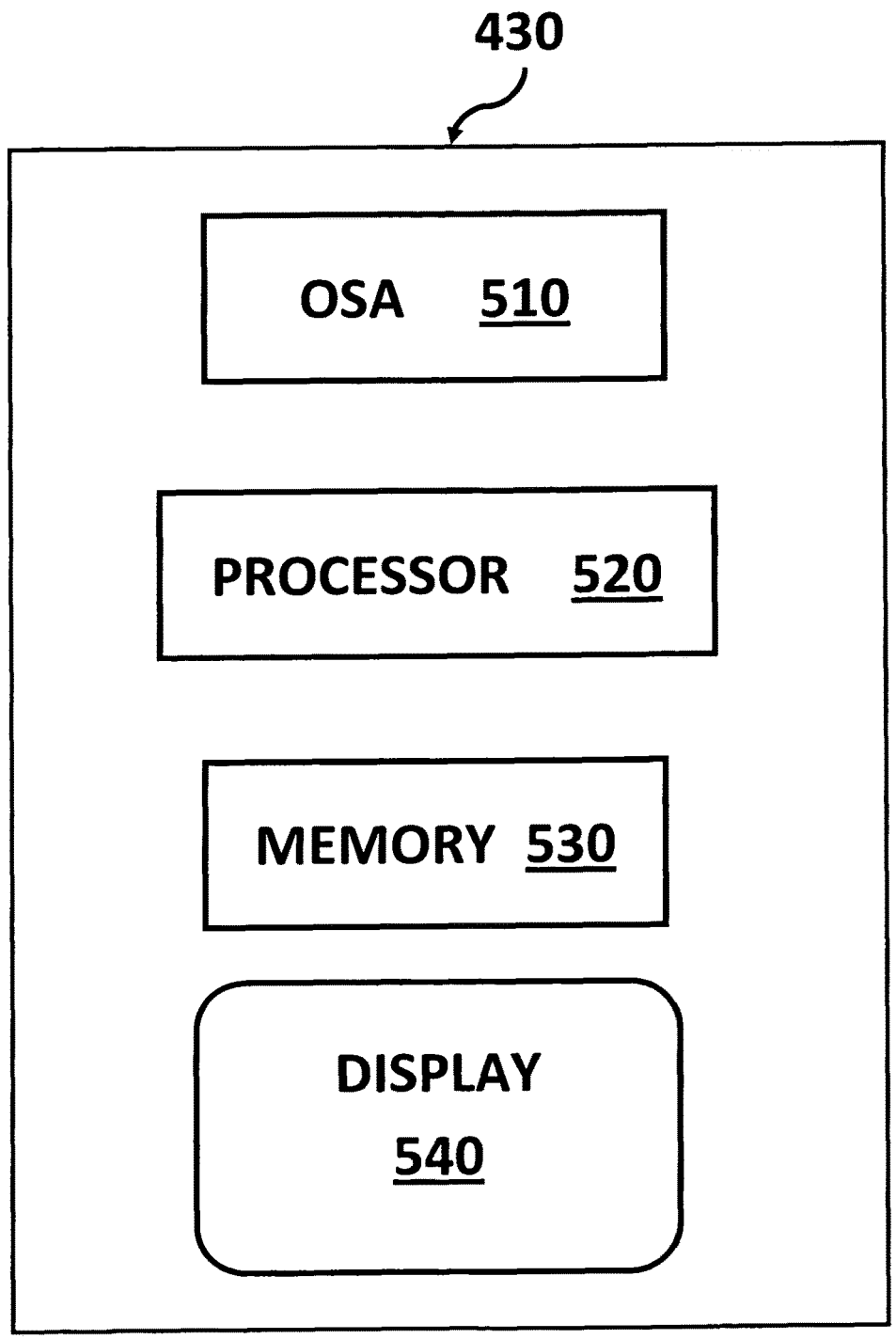
FIG. 5 is a functional block diagram of a detector used in the system of FIG. 4.

Referring to FIG. 4, shown is a functional block diagram of a system, generally indicated by 400, for detecting an element to be detected, in accordance with another embodiment. The system 400 has a light source 410 coupled to an optical sensor 420, and a detector 430. In some implementations the optical sensor 420 is the same as the optical sensor 200 of FIGS. 2A and 2B. The optical sensor 420 is partially enclosed by a container 440 and has end portions 451, 452 extending from container 440. The container has an input 461 and an output 462. The light source 410 is any suitable BBS (Broadband Source) such as an Agilent-83437A BBS, for example. With reference to FIG. 5, the detector has an OSA (Optical Spectrum Analyzer) 510, a processor 520, a display 540, and a memory 530 containing computer readable instructions executable by the processor for analyzing information provided by the OSA 510 and for displaying results from the analysis. The OSA 510 can be any suitable OSA such as an Agilent-86142B OSA with a resolution of 0.02 nm, for example.

The light source 410 provides light to the optical sensor 420, which propagates into the optical sensor 420. A liquid or solution enters the container 440 through the input 461 and exits the container 440 through the output 462 to provide a flow of the liquid or solution. In some implementations there is no flow of the liquid or solution. In implementations where *E. coli* bacteria is to be detected, *E. coli* bacteria present in the liquid or solution will bond to the optical sensor 420 and cause a change in the transmittance of the optical sensor 420. This change in the transmittance of the optical sensor 420 is detected by the detector 430.

Figure 6:
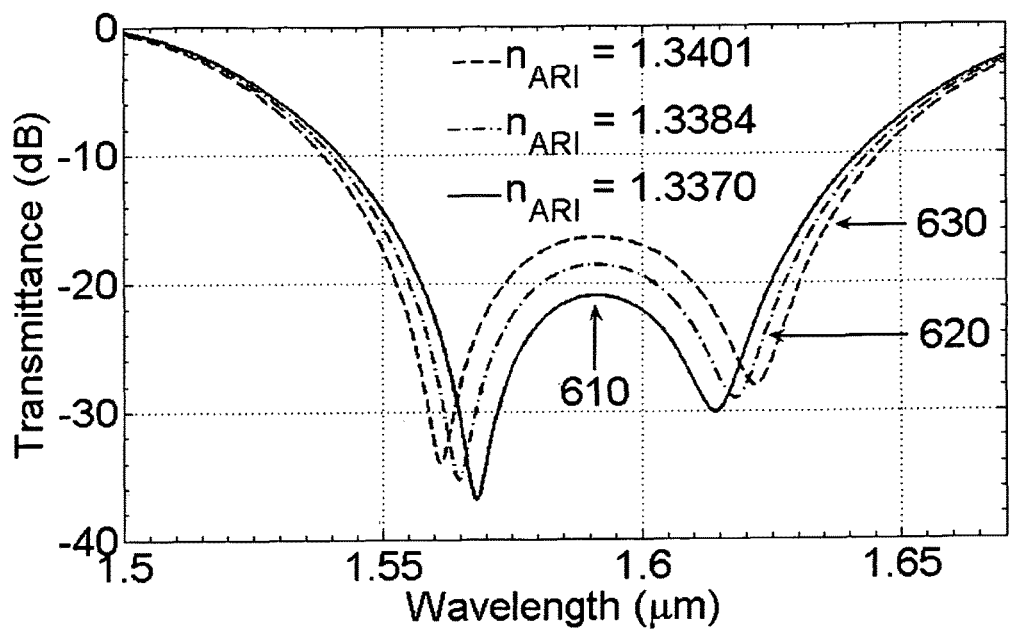
FIG. 6 is a plot of the transmittance of an optical sensor of FIG. 4 plotted as a function of wavelength of light propagating through the optical sensor.

The detector 430 can be calibrated by determining the ambient refractive index (ARI) sensitivity of the optical sensor 420 using a controlled experiment in which analytes of known refractive indices measured. The variations in the resonant wavelengths $\lambda_{Ri}$ of the optical sensor 420 are measured as a function of the refractive indexes. FIG. 6 is a plot of the transmittance of the optical sensor 420 plotted as a function of wavelength of light propagating through the optical sensor 420 of FIG. 4. Curves 610, 620, 630 are transmittance functions for $n_{ARI}$=1.3370, 1.3384, and 1.3401, respectively. The slope of the shift in position of each wavelength $\lambda_{Ri}$ as function of the ARI or equivalently the ARI sensitivity is approximately 2321.6 nm/RIU (Refractive Index Unit). The slope for the separation between the resonant wavelengths $\lambda_{Ri}$, as function of the ARI is twice that of the slope of the shift in position of the wavelengths $\lambda_{Ri}$ as function of the ARI. As such, the use of two resonance wavelengths provides a doubling in the sensitivity of the optical sensor 420.

Unlike adsorption-based measurements where the *E. coli* bacteria can be wiped away from the outer surface of an optical sensor by subsequent PBS buffer washes, with the optical sensor 420 the *E. coli* bacteria remain firmly attached to the optical sensor 420 due to the bacteriophages being covalently bonded, making the measurements stable in time. Given this stability the detector 430 is capable of measuring spectral shifts of the resonance wavelengths $\lambda_{Ri}$ as a function of concentration of *E. coli* bacteria. These spectral shifts are influenced not only by the changing refractive index of the solution but also by the change in the radius of the optical sensor 420 due to the *E. coli* bacteria being attached to the optical sensor 420. To a first-order approximation, the spectral shift in resonance wavelength $\Delta\lambda_R^m$ for mode m as a function of changes in the ARI $\Delta n_{ARI}$ and changes in the cladding radius $\Delta r_{cl}$ is given by:

$$\Delta\lambda_R^m = -\Lambda\left(\frac{\partial n_{eff}^{0m}}{\partial n_{ARI}}\Delta n_{ARI} + \frac{\partial n_{eff}^{0m}}{\partial r_{cl}}\Delta r_{cl}\right).$$

Figure 7A:
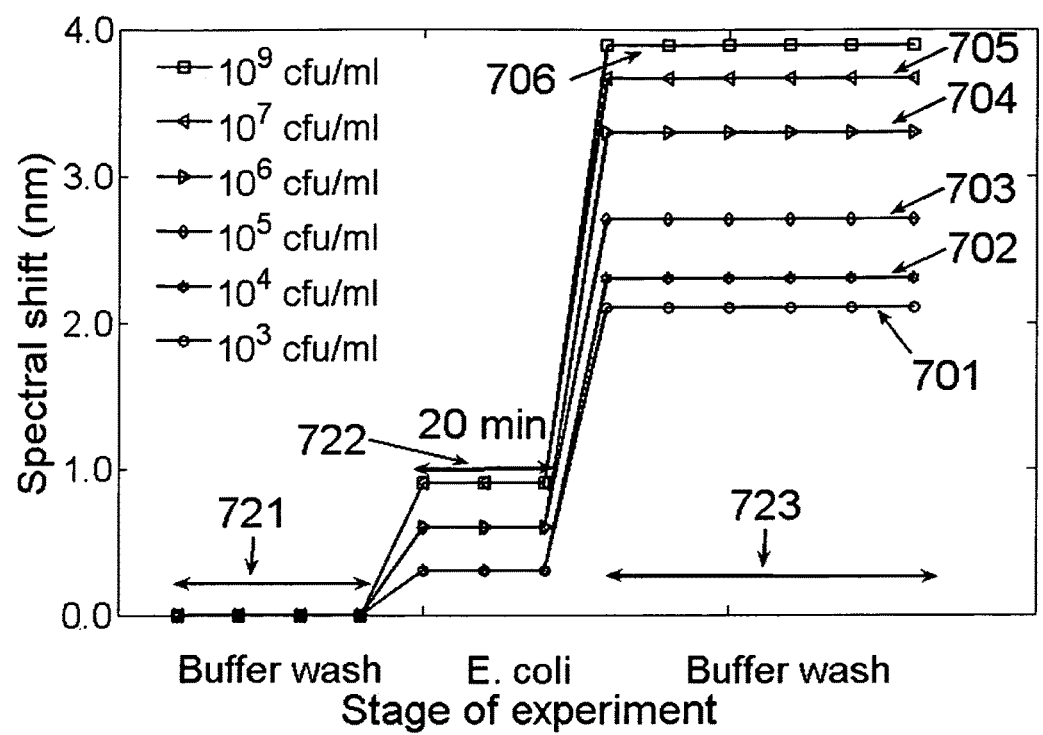
FIG. 7A is a plot of the spectral shift of the double resonant wavelengths for different stages of experiment and for different concentrations of *E. coli* bacteria; and, FIG. 7B is a plot of the spectral shift of the double resonant wavelengths as a function of the concentration of *E. coli* bacteria.
Figure 7B:
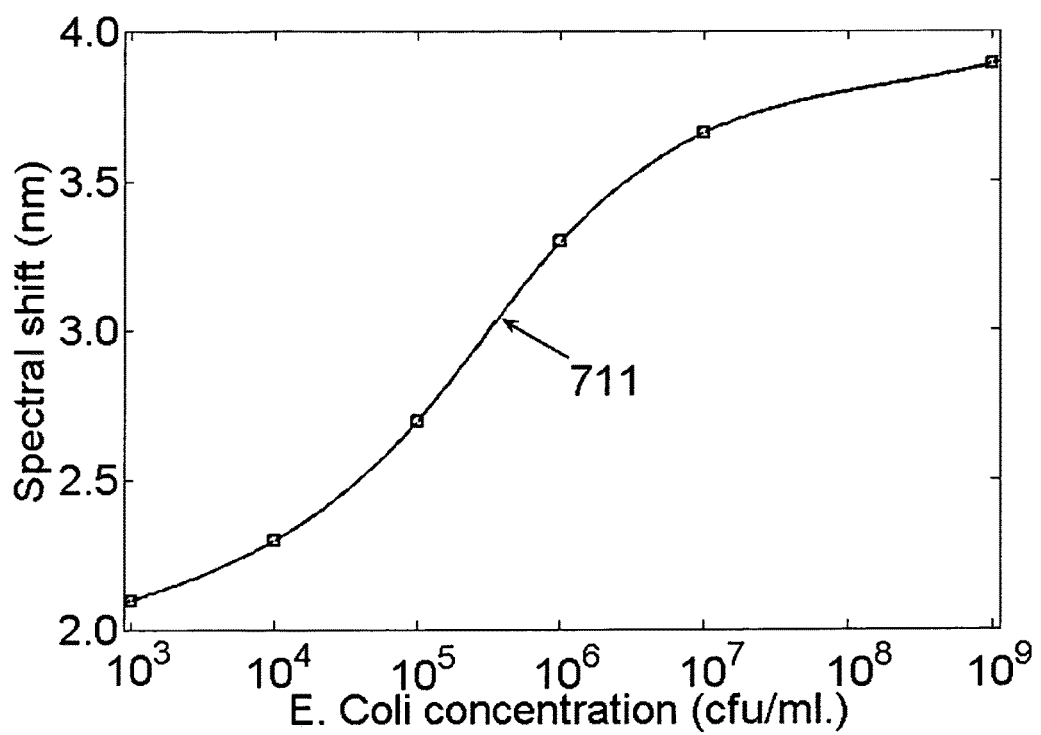

FIG. 7A is a plot of the spectral shift of the resonant wavelengths for different stages of experiment and for different concentrations of *E. coli* bacteria. There are three stages to the experiment: a first stage 721 which includes a buffer wash of the optical sensor 420; and second stage 722 where the optical sensor 420 is exposed to a solution containing *E. coli* bacteria; and a third stage 723 which includes a buffer wash of the optical sensor 420. Curves 701, 702, 703, 704, 705, 706 show the spectral shift for different concentrations of *E. coli* bacteria. The curves 701, 702, 703, 704, 705, 706 show a spectral shift in the wavelengths ARI of approximately 2 nm to 4 nm after the third stage 723 showing a clear dependence of the spectral shift as a function of *E. coli* bacteria concentration. FIG. 7B is a plot of the spectral shift of the resonant wavelengths as a function of the concentration of *E. coli* bacteria. A curve 711 shows that the spectral shift initially increases exponentially with increasing *E. coli* concentrations and then at a concentration of about $10^6$ cfu/ml-$10^7$ cfu/ml the spectral shift begins to level off with increasing concentration of *E. coli* bacteria. This leveling off can be explained. An increase in concentration of *E. coli* bacteria decreases the refractive index of the solution and at the same time results in an increase in the surface coverage of the optical sensor 420. At high *E. coli* concentrations, however, the sensor surface is almost completely covered with the *E. coli* bacteria and saturation effects begin to show in the spectral shift. The low spectral shifts in the resonant wavelengths at lower *E. coli* concentrations are primarily due to the smaller fractional surface coverage of the *E. coli* bacteria.

The time required to conduct measurements is about 20 minutes which is significantly lower than for prior art methods, which require about 24 hrs.

Embodiments have been described in the context of detection of *E. coli* bacteria. However, is it to be clearly understood that embodiments are not limited to detection of *E. coli* bacteria. For example, with reference to FIG. 2A any biophage can be covalently bonded at the surface 235 of the optical sensor 200 to produce the binding sites 130 for detection of a respective bioagent. More generally, any suitable element capable of binding to another element to be detected can be covalently bonded to the surface 235 of the optical sensor 200 to form the binding sites 230. For example, in some implementations synthetic DNA is covalently bonded to the surface 235 of the cladding 220 and the synthetic DNA forms the binding sites 230 for binding to certain viruses or certain molecules. In yet other implementations, Palladium is covalently bonded to the surface 235 of the cladding 220 to form crystal structures which in turn form the binding sties 230 for binding with hydrogen. The crystal structures expand as hydrogen binds to them resulting in spectral shifts in the resonant wavelengths of the optical sensor 200. In some implementations the optical sensor 200 has more than one type of binding site for detections of more than one type of element.

In the optical sensor 200, the binding sites 230 are covalently bonded to the surface 235 of the cladding 220. However, it is to be clearly understood that embodiments are not limited to covalent bonding and other mechanisms, such as adsorption for example are possible. Furthermore, although the grating 240 is an LPFG it is to be clearly understood that embodiments are not limited to LPFGs and that in some embodiments other gratings are used. Embodiments have been described with one split resonance having two resonant wavelengths. More generally, in embodiments the optical sensors have none or more split resonance each with two resonant wavelengths. Advantageously, optical sensors with one or more split resonance can benefit from a greater sensitivity.

The embodiments presented are exemplary only and persons skilled in the art would appreciate that variations to the embodiments described above may be made without departing from the spirit of the present disclosure. The scope is solely defined by the appended claims.

We claim:

1. Use of an optical sensor capable of providing at least one split resonance in measuring spectral shifts in resonance wavelengths of the at least one split resonance to detect one or more elements in a water-based solution to be detected using said spectral shifts, the optical sensor comprising:
   a waveguide having a circular core, a circular cladding having an outer surface and a long period fiber grating, the waveguide having a portion along its length including the circular core, the circular cladding and the long period fiber grating with the long period fiber grating having a single grating period within said portion of the waveguide, the circular core, the circular cladding and the long period fiber grating within said portion of the waveguide being tuned to collectively excite at least one cladding mode, each of the at least one cladding mode having a corresponding one of the at least one split resonance with two resonant wavelengths; and
   binding sites on the outer surface of the circular cladding for binding to the elements to be detected to the outer surface of the circular cladding.

2. An optical sensor to detect one or more elements in a water-based solution comprising:
   a waveguide having a core, a cladding having an outer surface and a long period fiber grating, the waveguide having a portion along its length including the core, the cladding and the long period fiber grating with the long period fiber grating having a single grating period within said portion of the waveguide, the core, the cladding and the long period fiber grating within said portion of the waveguide being tuned to collectively excite at least one cladding mode in the water-based solution, each of the at least one cladding mode having a corresponding one of at least one split resonance with two resonant wavelengths; and binding sites covalently bonded on the outer surface of the cladding for binding to elements to be detected to the outer surface of the cladding.

3. An optical sensor according to claim 1 wherein the cladding is thinned down to a thickness sufficiently low to produce the at least one split resonance.

4. An optical sensor according to claim 1 wherein the binding sites comprise a biophage.

5. An optical sensor according to claim 1 wherein the binding sites comprise a bacteriophage.

6. An optical sensor according to claim 1 wherein the binding sites comprise Palladium.

7. An optical sensor according to claim 1 wherein the binding sites comprise synthetic DNA.

8. An optical sensor according to claim 1 wherein the binding sites comprise at least two different types of binding sites capable of binding to different types of elements.

9. A method of fabricating an optical sensor, to detect one or more elements in a water-based solution, having a waveguide with a circular core, a circular cladding having an outer surface and a grating, the waveguide having a portion along its length including the circular core, the circular cladding and the grating with the grating having a single grating period within said portion of the waveguide, the method comprising:

etching the circular cladding at the outer surface within said portion of the waveguide to thin the circular cladding down to a thickness sufficiently low to excite a cladding mode when the optical sensor is immersed in the water-based solution, the cladding mode having a split resonance with two resonant wavelengths.

10. A method according to claim 9 comprising:
covalently bonding binding sites to the outer surface of the circular cladding for allowing elements to be detected to bind to the outer surface of the circular cladding.

11. A method according to claim 9 wherein the grating is a long period fiber grating.

12. A system for detecting an element to be detected in a water-based solution, the system comprising:

an optical sensor comprising:
  a waveguide having a circular core, a circular cladding having an outer surface and a long period fiber grating, the waveguide having a portion along its length including the circular core, the circular cladding and the long period fiber grating with the long period fiber grating having a single grating period within said portion of the waveguide, the circular core, the circular cladding and the long period fiber grating within said portion of the waveguide being tuned to collectively excite at least one cladding mode in the water-based solution, each of the at least one cladding mode having a corresponding one of at least one split resonance with two resonant wavelengths; and
  binding sites on the outer surface of the circular cladding for binding to the element to be detected to the outer surface of the circular cladding;

a light source coupled to the optical sensor for providing light to the optional sensor; and, a detector coupled to the optical sensor for receiving said light after transmission through the optical sensor, measuring spectral shifts in the two resonance wavelengths of the at least one split resonance, and detecting the element to be detected using said spectral shifts.

* * * * *